United States Patent [19]

Michels et al.

[11] Patent Number: 5,322,073
[45] Date of Patent: Jun. 21, 1994

[54] FEEDING TUBE RETAINING STRAP

[75] Inventors: Lester D. Michels, Eden Prairie; Douglas J. Duchon, Chanhassen; Norman C. Reid, Minneapolis, all of Minn.

[73] Assignee: Sandoz Ltd., Basel, Switzerland

[21] Appl. No.: 828,398

[22] Filed: Jan. 30, 1992

[51] Int. Cl.⁵ .................. A61B 19/00; A61F 5/37
[52] U.S. Cl. ...................... 128/869; 128/876
[58] Field of Search ............. 128/876, 877, 878, 879, 128/869; 606/234, 235, 236; 2/49 R, 50

[56] References Cited

U.S. PATENT DOCUMENTS

| 954,066 | 4/1910 | Ware | 606/236 |
|---|---|---|---|
| 2,451,718 | 10/1948 | Corrao | 2/49 R |
| 2,631,288 | 3/1953 | Daust | 2/49 R |
| 4,473,907 | 10/1984 | Maillard | 2/49 R |
| 4,610,244 | 9/1986 | Hammond | 128/876 |
| 4,719,650 | 1/1988 | Milloy | 2/49 R |
| 4,994,075 | 2/1991 | Smith | 606/235 |
| 4,994,076 | 2/1991 | Guss | 606/236 |
| 5,049,127 | 9/1991 | Yen Tseng | 606/236 |
| 5,083,575 | 1/1992 | Jones | 128/877 |
| 5,086,517 | 2/1992 | Jones | 2/49 R |

*Primary Examiner*—Michael A. Brown
*Attorney, Agent, or Firm*—Robert S. Honor; Melvyn M. Kassenoff; Carl W. Battle

[57] ABSTRACT

Retaining device for patient feeding set to prevent unintentional disconnect of the feeding solution supply tube from the feeding tube.

5 Claims, 2 Drawing Sheets

FEEDING TUBE RETAINING STRAP

FIELD OF THE INVENTION

This invention relates to retaining devices, in particular, it relates to retaining devices for securing patient feeding tube to feeding supply tubes.

BACKGROUND AND SUMMARY OF THE INVENTION

One of the problems associated with patient feeding, whether enteral or parenteral feeding, is the unintentional disconnect of the feeding supply tube from the connector of an enteral or parenteral feeding tube.

This invention provides a retaining device for preventing the unintentional disconnect of a feeding solution supply tube from the connector of a feeding tube by providing a flexible locking strap on the connector, wherein the strap has an opening in which the supply tube is removably secured to prevent unintentional disconnect of the supply tube from the connector.

The connector may be a commercial connector device which provides retention of the union between the female connector part on the feeding tube, and a male (luer) dispensing tip on the supply tube.

The connector may also be a Y-port connector in which one or both of the main or secondary ports may have the retaining device of this invention.

The retaining device may also contain a plug normally used for stoppering the port of the connector.

DESCRIPTION OF THE PREFERRED EMBODIMENTS

The retaining device of this invention will be described with relation to a Y-port connector.

Figure 1:
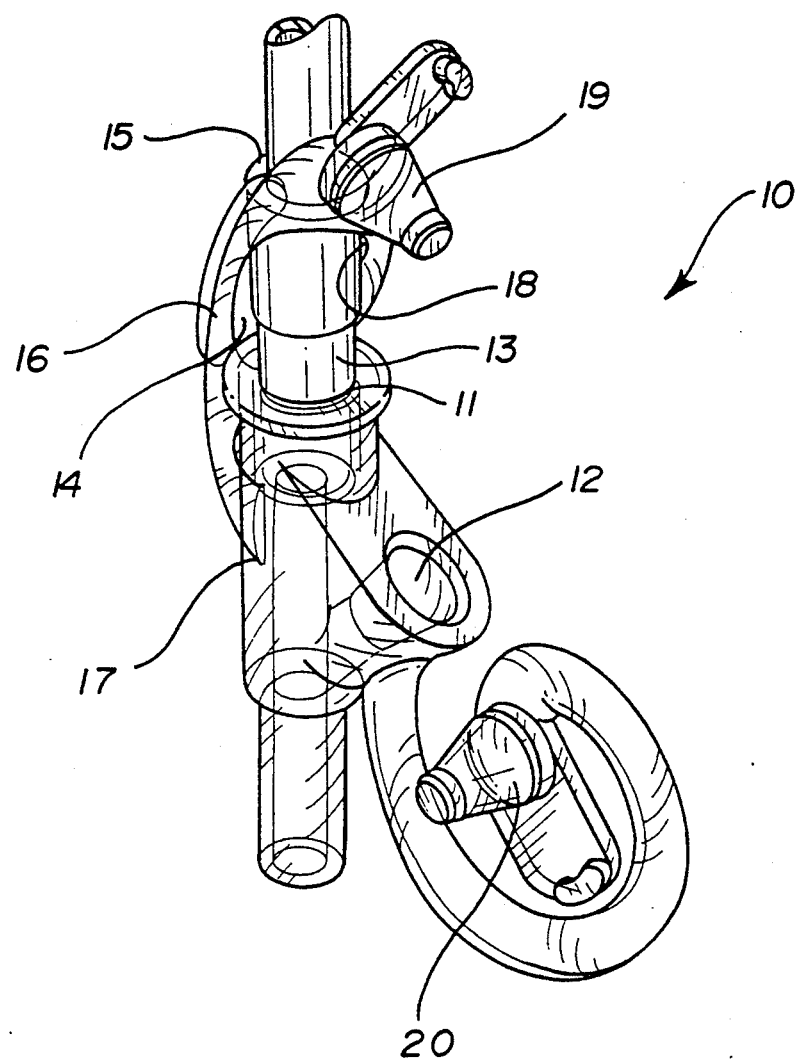
FIG. 1 is an isometric view of the retaining device of this invention, shown retaining a feeding supply tube in a Y-port connector.
Figure 2:
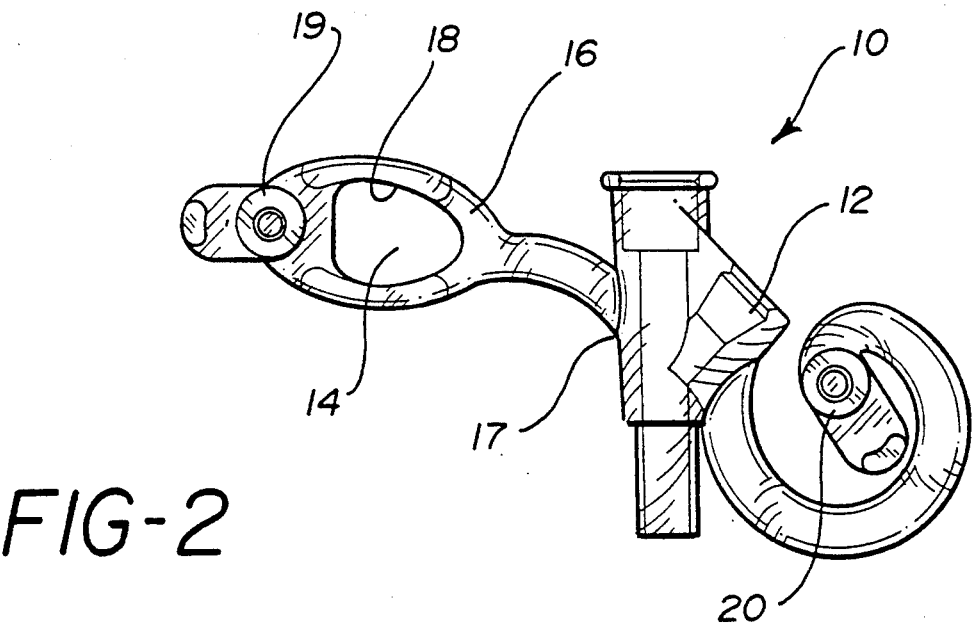
FIG. 2 is a side elevation of the device of FIG. 1 in a non-retaining mode.

Referring now to FIG. 1, there is shown a Y-port connector 10, having a main port 11 and a secondary port 12. A feeding supply tube 13 is in union with the connector 10 after being passed through an opening 14 in the flexible locking strap 16. The strap 16 is secured at one end 17 to the connector 10 (see FIG. 2). The locking strap 16 holds the supply tube 13 secure in the connector 10 by frictional engagement between the wall 18 of the opening 14 and the surface of the supply tube 13. The engagement may be on the lip 15 of the connecting end of the supply tube 13.

The locking strap 16 is shown with a plug 19 normally used for stoppering the main port 11 when the supply tube 13 is not in place in the port.

Also attached to the connector 10 is a conventional plug 21 secured to the connector 10. It is understood that the locking strap 16 with a plug 19 may also be used on the secondary port 12 to secure any tubing which may be inserted in the port 12.

To secure a supply tube 13 to the connector 10, the opening 14 in the locking strap 16 is stretched over the main port 11, and the supply tube 13 passed through the hole 14 in the main port 11. When the supply tube 13 is conventionally secured in the main port 11, the wall 18 of the opening 16 is allowed to frictionally engage the lip 15 on the supply tube 13 to secure it in place to prevent unintentional disconnect from the main port 11.

Materials having the desired flexibility for the locking strap 16, e.g., polyvinylchloride and the like may be used in making the strap.

We claim:

1. A retaining device on a connector of a feeding tube for preventing unintentional disconnect of a feeding solution supply tube from said connector, wherein said retaining device comprises a flexible locking strap secured to said connector and having an opening in said strap; said strap being adapted for having said supply tube passed through said opening and removably secured by engagement of said supply tube and said opening to prevent unintentional disengagement of said supply tube from said connector, and wherein said connector is a Y-port connector.

2. The device according to claim 1 in which said locking strap contains a plug adapted for stoppering a port of said connector.

3. The device of claim 2 wherein said connector is a female connector and said supply tube has a male dispensing tip.

4. The device of claim 1 wherein said engagement of said supply tube and said opening is by frictional engagement.

5. The device of claim 1 wherein said engagement of said supply tube and said opening is by a lip on the connecting end of said supply tube.

* * * * *